United States Patent
Jakoby et al.

(10) Patent No.: US 6,938,462 B2
(45) Date of Patent: Sep. 6, 2005

(54) DEVICE FOR MEASURING VISCOSITY AND/OR DENSITY

(75) Inventors: Bernhard Jakoby, Vienna (AT); Johannes Artzner, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/501,818

(22) PCT Filed: Sep. 23, 2002

(86) PCT No.: PCT/DE02/03565
§ 371 (c)(1), (2), (4) Date: Dec. 22, 2004

(87) PCT Pub. No.: WO03/060482
PCT Pub. Date: Jul. 24, 2003

(65) Prior Publication Data
US 2005/0103096 A1 May 19, 2005

(30) Foreign Application Priority Data
Jan. 18, 2002 (DE) .......................................... 102 03 475

(51) Int. Cl.⁷ ............................ G01N 9/24; G01N 11/16
(52) U.S. Cl. .................... 73/54.02; 73/54.24; 73/54.25; 73/54.26; 73/54.27; 73/54.41; 73/32 A; 73/579
(58) Field of Search ............................. 73/32 A, 54.02, 73/54.23, 54.24, 54.25, 54.26, 579, 54.27, 54.41, 61.79, 64.53

(56) References Cited

U.S. PATENT DOCUMENTS

| | | | |
|---|---|---|---|
| 4,023,400 A | 5/1977 | November | .................. 73/32 A |
| 4,783,987 A | 11/1988 | Danielson et al. | .......... 73/32 A |
| 4,788,466 A | 11/1988 | Beeler et al. | .......... 310/323.06 |
| 5,054,313 A | 10/1991 | Fitzgerald et al. | ......... 73/54.27 |
| 5,416,448 A | 5/1995 | Wessendorf | |
| 5,741,961 A | 4/1998 | Casaus et al. | .............. 73/32 R |

FOREIGN PATENT DOCUMENTS

| | | | |
|---|---|---|---|
| DE | 198 50 803 | 5/2000 | |
| WO | WO 00/25 118 | 5/2000 | ................ 73/54.41 |

OTHER PUBLICATIONS

Barnes, C., "Development of Quartz Crystal Oscillators for Under–Liquid Sensing", Sensors and Actuators A, Elsevier Sequoia S.A., Lausanne, Ch., vol. A29, No. 1, Sep. 1, 1991, pp. 59–59.

Chagnard, C. et al., "An Electronic Oscillator with Automatic Gain Control: EQCM Applications", Sensors and Actuators B, Elsevier Sequoia S.A., Lausanne, CH, vol. B32, No. 2, May 1, 1996, pp. 129–136.

*Primary Examiner*—Daniel S. Larkin
(74) *Attorney, Agent, or Firm*—Kenyon & Kenyon

(57) ABSTRACT

A device for measuring the viscosity and/or the density of a fluid using a resonator capable of mechanical vibrations. The resonator is capable of being brought into contact with the fluid. An oscillator circuit is also provided, wherein the oscillator circuit has a first feedback network and a second feedback network.

7 Claims, 1 Drawing Sheet

DEVICE FOR MEASURING VISCOSITY AND/OR DENSITY

FIELD OF THE INVENTION

The present invention relates to a device for measuring the density and/or the viscosity of a fluid.

BACKGROUND INFORMATION

A sensor system and a method for ascertaining the density and the viscosity of a fluid are described in German Patent Application No. DE 198 50 803. In this application, the use of at least one oscillating circuit is described.

SUMMARY

An example device according to the present invention may have the advantage that the possibility is created for compensating for effects which impair the result of the measurement.

It is especially advantageous if the first feedback network is provided as a feedback network having a resonator functioning as a sensor element, as the frequency-determining element, and that the second feedback network is provided as a feedback network having a correction capacitance as the frequency-determining element. It is possible thereby that, when measuring the viscosity of highly viscous liquids, a capacitance lying essentially parallel to the detection impedance, for example, in the form of stray capacities, is able to be compensated for. Because of that, a compensation is possible for the parallel-lying capacitance, without having to rely, for the compensation, on components having bad, i.e., large temperature coefficients or bad drift properties, such as, for instance, inductive components.

It may also be an advantage if the device has an amplifier, that the amplifier has a first input, and that the first input of the amplifier has supplied to it an output of the first feedback network and an output of the second feedback network, the difference of the outputs of the feedback networks being supplied to the first input of the amplifier. This makes possible in a simple manner the compensation of the parallel-lying capacitances, in that the correction capacitance is selected to be approximately as great as the capacitances to be corrected and lying parallel.

BRIEF DESCRIPTION OF THE DRAWINGS

An exemplary embodiment of the present invention is illustrated in the following figures, and explained in detail in the following description.

DETAILED DESCRIPTION OF AN EXAMPLE EMBODIMENT

It is generally known that one may use piezoelectric resonators, particularly thickness shear resonators, and in particular made of quartz, for measuring viscosity and or density. If such a thickness shear resonator is dipped into a viscous fluid, the resonant frequency of the natural oscillation and its damping change as a function of the viscosity and the density of the liquid.

Figure 3:
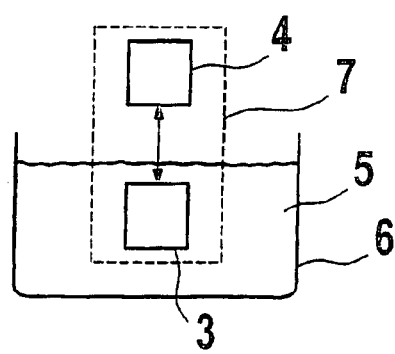
FIG. 3 shows a schematic representation of a measuring system having a device according to the present invention.

For the sake of simplicity, FIG. 3 is first described. FIG. 3 shows a schematic representation of a measuring apparatus having an example device according to the present invention. In a container 6 there is a fluid 5, especially a liquid 5, according to the present invention. The resonator denoted by reference numeral 3 is dipped into liquid 5 or fluid 5. Resonator 3 is connected to a regulating and evaluation unit 4, which is in a position to pass on the measurement results with respect to the variables to be measured of liquid 5 via channels (not shown) that are wire-bound or not wire-bound. Resonator 3 and regulating and evaluation unit 4 together form the example device according to the present invention, that is denoted by reference numeral 7, for measuring the viscosity and/or density of a liquid. This is shown in FIG. 3 by a combination of resonator 3 and regulating and evaluation unit 4, shown by a dotted line and provided with reference numeral 7.

Figure 1:
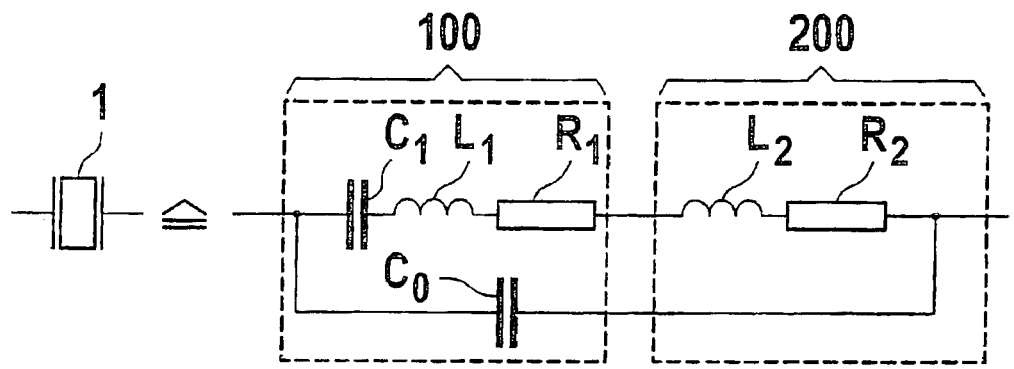
FIG. 1 shows a substitute circuit diagram of a quartz resonator in the vicinity of the resonant frequency.
Figure 2:
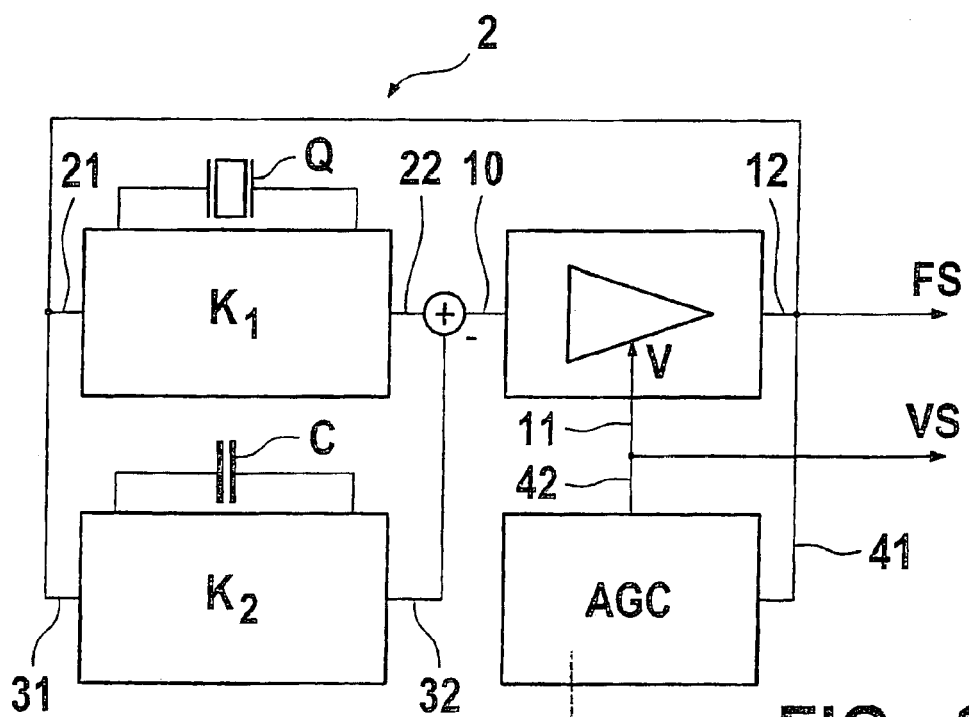
FIG. 2 shows a block diagram of an example oscillator circuit.

FIGS. 1 and 2 are now described below.

In this context, the substitute circuit diagram shown in FIG. 1 applies to a quartz resonator. This indicates that a circuit symbol for the resonating system shown in the left part of FIG. 1 and furnished with reference numeral 1, made up of resonator 3 and fluid 5 engaged with it, corresponds to a resonating system made up of a first part denoted by reference numeral 100 in FIG. 1, which is also designated below as "dry portion", and a second part denoted by reference numeral 200, which is also designated below as "liquid portion" or "fluid portion".

Dry portion 100 and fluid portion 200 are shown in FIG. 1 as being connected in the sense of a series connection, and are arranged in the right part of FIG. 1 one behind the other. Dry portion 100 in this case includes a resonator 3, whose behavior may be described by a first capacitance $C_1$, a first inductance $L_1$ and a first resistor $R_1$. Fluid portion 200 includes, in this case, the fluid layer bordering on resonator 3 or the portion of the fluid which is influenced by the mechanical vibrations of the resonator. The behavior of the fluid layer engaged with resonator 3 or of the portion of the fluid engaged with resonator 3 may be described, in this context, by a second inductance $L_2$ and a second resistor $R_2$.

Second resistor $R_2$ is approximately proportional to the square root of the product of the density and the dynamic viscosity of the fluid or liquid. Second resistor $R_2$ represents the viscous damping by the liquid. Second inductance $L_2$ brings about a frequency shift by the viscous liquid, second inductance $L_2$, at rough resonator surfaces, also including portions that are created by liquid portions "trapped" in the rough resonator surface. This frequency shift is also approximately proportional to the square root of the product of the density and the dynamic viscosity of the fluid or liquid. At a known, or sufficiently constant density, the resonator may therefore be used to determine the (dynamic) viscosity. According to the present invention, for evaluation or for measurement it is provided that the electrical parameters used are recorded by using the resonator as frequency-determining element in an oscillator circuit, or rather by it.

In the characterization of highly viscous liquids, second resistor $R_2$ rises greatly, so that the impedance of the resonator is also determined in the vicinity of the series resonant frequency generally by a capacitance that is present in parallel to the serial arrangement made up of first capacitance $C_1$, first inductance $L_1$, first resistor $R_1$, second inductance $L_2$ and second resistor $R_2$ and that is designated by reference numeral $C_0$. This capacitance $C_0$ represents the electrostatic capacitance which is manifested by the electrodes applied to the resonator for the excitation of the oscillation. Additional stray capacitances, which are not shown in FIG. 1 for simplicity's sake, and which also lie parallel to capacitance $C_0$, may also be present. The stray capacitances represent, for example, those capacitances which are manifested by the supply lines to the sensor element.

In response to high resistance values of second resistor $R_2$, that is, at high viscosities of the liquid, the overall impedance of the resonator is also determined in the vicinity of the series resonant frequency, generally by capacitance $C_0$ (or rather, with the addition of the stray capacitances), whereby the determination of the relevant substitute parameters using an oscillator circuit becomes more difficult.

A possible remedy is the parallel connection of an inductance for compensating capacitance $C_0$, or rather, with the addition of the stray capacitances, in the vicinity of the series resonant frequency of the resonator. The disadvantage of this is, on the one hand, the required adjustment of this additional (compensating) inductance and, on the other hand, the usually bad temperature coefficients or drift properties of inductive component parts.

According to the present invention, an oscillator circuit is provided in which the interfering influence of capacitance $C_0$ is suppressed by the use of a reference capacitance C, which is also denoted below as correction capacitance C. In the simplest case, this reference capacitance C should have approximately the value of capacitance $C_0$. What is advantageous, according to the present invention, is the possibility of compensation of capacitance $C_0$ without the need for an inductance to be adjusted, and accordingly of the dropping out of all the disadvantages connected with that.

FIG. 2 shows a block diagram of an oscillator circuit 2 according to the present invention. Oscillator circuit 2 has an amplifier V, a first feedback network $K_1$, a second feedback network $K_2$ and an amplification regulating unit AGC. Amplifier V has a first input 10, a second input 11 and an output 12. The first feedback network $K_1$ has an input 21 and an output 22. The second feedback network $K_2$ has an input 31 and an output 32. The amplification regulating unit AGC has an input 41 and an output 42. Output 12 of amplifier V is connected to both input 21 of first feedback network $K_1$ and to input 31 of second feedback network $K_2$ and to input 41 of amplification regulating unit AGC. The output of first feedback network $K_1$ is connected to first input 10 of the amplifier. The output of second feedback network $K_2$ is also connected to first input 10 of the amplifier. According to the present invention, it is provided in particular that output 32 of second feedback network $K_2$ is connected to first input 10 of amplifier V in such a way that output 32 of second feedback network $K_2$ works negatively on first input 10 of amplifier V in such a way that the difference of outputs 22, 32 of first and second feedback networks $K_1$, $K_2$ is present at first input 10 of amplifier V. This is shown in FIG. 2 by designating output 32 of second feedback network $K_2$ with a minus sign (−), in the vicinity of the joining together the signals of outputs 22, 32 of feedback networks $K_1$, $K_2$.

Oscillator circuit 2 includes amplifier V and feedback network $K_1$, which includes the resonator, furnished in FIG. 2 with reference symbol Q, as the frequency-determining element. Resonator Q, according to the present invention, is provided especially as quartz, and is indeed designated below as quartz Q. The transmission coefficient of feedback network $K_1$ is typically of such a nature that, in the vicinity of the series resonant frequency of quartz Q, its absolute value is a maximum. At the same time, in the vicinity of this point, advantageously the phase condition for the oscillation should be satisfied, i.e., it should be true that the sum of the phases of first feedback network $K_1$ and amplifier V is a multiple of 360°. The last-mentioned conditions may be fulfilled by the appropriate design of the circuit blocks of first feedback network $K_1$, second feedback network $K_2$ and amplifier V.

The oscillation takes place at a frequency of $\omega$, at which the oscillating condition is satisfied; in the case of the system shown in FIG. 2 this means that the product of the transmission coefficient of amplifier V, multiplied by the difference that results from transmission coefficient of first feedback network $K_1$ reduced by the transmission coefficient of second feedback network $K_2$, should be exactly 1. The transmission coefficients of the functional blocks of oscillator circuit 2 should be viewed, in this case, as transmission coefficients of a complex variable, and therefore these oscillating conditions may be split up into an amplitude condition and a phase condition.

Because of amplification regulating unit AGC, the amplitude condition may be satisfied at the oscillating frequency specified by the phase condition. Amplification regulating unit AGC includes, for example, a functional block not shown in FIG. 2 for simplicity's sake for recording the amplitude of oscillation of a first output signal of oscillator circuit 2 shown in FIG. 2 as having reference symbol FS, which, according to the present invention, corresponds particularly to the output signal of amplifier V. This functional block in amplification regulating unit AGC for recording the amplitude of oscillation is in particular designed as a rectifier circuit. In addition, amplification regulating unit AGC may include, for example, a controller (not shown in FIG. 2 for simplicity's sake) which, via output 42 of amplification regulating unit AGC, sets the amplification in amplifier V in such a way that a constant oscillating amplitude comes about. A second output signal of oscillator circuit 2 shown in FIG. 2 by reference symbol VS corresponds to output 42 of amplification regulating unit AGC.

According to the present invention, in response to the regulation by the oscillating circuit, it is the aim to bring about an oscillation at the series resonant frequency determined by the impedance to be measured, the impedance to be measured being given by the series circuit, shown in FIG. 1, made up of first inductance $L_1$, first capacitance $C_1$, first resistor $R_1$, second inductance $L_2$ and second resistor $R_2$. The oscillator frequency, which is essentially determined, after compensation has taken place, by inductances $L_1$ and $L_2$ and first capacitance $C_1$, and for which the first output signal FS is a measure, may then be used to determine second inductance $L_2$. Since second resistor $R_2$, which is designated below also as loss resistor $R_2$, determines the damping of first feedback network $K_1$, it may be determined directly by the second output signal VS of the oscillating circuit, which is necessary for bringing about the oscillation, determines the amplification, and is denoted below also as amplification signal VS. Since both quantities, second inductance $L_2$ and second resistor $R_2$, are determined by the product of (dynamic) viscosity and density of the fluid, output signals FS and VS may be drawn upon for the determination of these liquid properties.

Without the presence of second feedback network $K_2$, the frequency-determining phase condition would, however, be considerably influenced by capacitance $C_0$, which is denoted below also as static capacitance $C_0$. This is true especially at large loss resistors $R_2$, which make the series resonant branch highly resistive. Consequently, at the total impedance of the oscillating system, static capacitance $C_0$ leads to a phase shift in the frequency response of first feedback network $K_1$, whereby the oscillating frequency moves away from the desired series resonant frequency or, in the extreme case, is interrupted. Upon deviation from the series resonant frequency, one is no longer able, without error, to infer the loss resistance $R_2$ from second output signal VS, which is supplied by amplification regulating unit AGC. To be sure, static capacitance $C_0$ could be compensated by a parallel inductance; however, this would involve severe disadvantages, such as:

- inductances are difficult to tune, and are able to be manufactured only under large manufacturing tolerances;
- inductance values of coils drift, and have temperature dependencies;
- the compensation takes place only at parallel resonant frequencies, given by static capacitance $C_0$ and the inductance that is connected in parallel.

The compensation method, according to the present invention, of static capacitance $C_0$ (and possibly present parallel stray capacitances present parallel thereto) is based on the assumption that first feedback network $K_1$ has a transmission coefficient which is at least approximately proportional to the inverse of the impedance of quartz Q. In this case, the proportion of static capacitance $C_0$ may be compensated by second feedback network $K_2$ that is situated parallel to first feedback network $K_1$, in that the output signals of first feedback network $K_1$ and of second feedback network $K_2$ are subtracted, as shown in FIG. 2. If feedback networks $K_1$, $K_2$ are chosen to be identical, then, for a complete compensation of static capacitance $C_0$, correction capacitance C has to be set to the value of static capacitance $C_0$. The functionality of second feedback network $K_2$ is comparable to that of first feedback network $K_1$ inasmuch as second feedback network $K_2$ also has a transmission coefficient which is essentially proportional to the inverse of an impedance, namely the impedance of correction capacitance C.

Instead of the exact adjustment of correction capacitance C to the value required for the optimum compensation, the compensation may advantageously also take place by the variation of other parameters which influence the transmission coefficient of second feedback network $K_2$, such as amplification factors.

One advantageous circuit technology execution of the oscillating circuit according to the present invention or of device 7 according to the present invention, uses with respect to ground, i.e., the reference potential of the oscillating circuit, which for simplicity's sake is not shown in FIG. 2, symmetrical signals, whereby the subtraction of output signals 22, 32 of feedback networks $K_1$, $K_2$ is able to take place by "crossing out" the signal lines. The execution of outputs 22, 32 of feedback networks $K_1$, $K_2$ in the form of so-called current outputs may in addition make possible a simple execution of the addition node, which is shown in FIG. 2 by a plus sign (+) in a circle, at the coming together of outputs 22, 32 of feedback networks $K_1$, $K_2$ to input 10 of the amplifier. Just such a design of outputs 22, 32 in the form of current outputs makes it alternatively also possible to carry out the subtraction, according to the present invention, of the output signal of second feedback network $K_2$ from the output signal of first feedback network $K_1$, using a subtraction node (not shown) instead of the addition node.

What is claimed is:

1. A device for measuring at least one of a viscosity of a fluid and a density of the fluid, the device comprising:
   a resonator capable of mechanical vibrations and capable of being brought into contact with the fluid; and
   an oscillator circuit including a first feedback network and a second feedback network;
   wherein the first feedback network includes the resonator, the resonator functioning as a frequency-determining element, whereby the resonator functions as a sensor for generatng a signal representative of at least one of the viscosity of the fluid and the density of the fluid, and wherein the second feedback network includes a correction capacitance as a frequency-determining element.

2. A device for measuring at least one of a viscosity of a fluid and a density of the fluid, the device comprising:
   a resonator capable of mechanical vibrations and capable of being brought into contact with the fluid, wherein the resonator functions as a sensor for generating a signal representative of at least one of the viscosity of the fluid and the density of the fluid;
   an oscillator circuit including a first feedback network and a second feedback network; and
   an amplifier having a first input, wherein a difference of an output of the first feedback network and an output of the second feedback network is supplied to the first input of the amplifier.

3. The device as recited in claim 2, wherein the amplifier has an output, the amplifier output being connected to an input of the first feedback network and an input of the second feedback network.

4. The device as recited in claim 3, wherein the amplifier output corresponds to a first output signal of the oscillator circuit.

5. The device as recited in claim 4, further comprising:
   an amplification regulating unit including an input, the amplifier output being connected to the input of the amplification regulating unit.

6. The device as recited in claim 5, wherein the amplifier has a second input and the amplification regulating unit has an output, the output of the amplification regulating unit being connected to the second input of the amplifier.

7. The device as recited in claim 5, wherein the output of the amplification regulating unit corresponds to a second output signal of the oscillator circuit.

* * * * *